United States Patent [19]

Yagi et al.

[11] Patent Number: 5,552,157
[45] Date of Patent: Sep. 3, 1996

[54] LIPOSOME FOR ENTRAPPING GENE, LIPOSOMAL PREPARATION AND PROCESS FOR THE MANUFACTURE OF THE PREPARATION

[75] Inventors: Kunio Yagi; Hitoshi Noda, both of Aichi-ken; Nobuko Ohishi, Gifu; Masayasu Kurono, Mie-ken, all of Japan

[73] Assignee: Kabushiki Kaisha Vitamin Kenkyusya, Gifu-ken, Japan

[21] Appl. No.: 412,107

[22] Filed: Mar. 28, 1995

Related U.S. Application Data

[60] Continuation of Ser. No. 84,629, Jun. 30, 1993, abandoned, which is a division of Ser. No. 750,125, Aug. 26, 1991, abandoned.

[30] Foreign Application Priority Data

Aug. 27, 1990 [JP] Japan .................................. 2-222553

[51] Int. Cl.$^6$ .............................. A61K 9/27; C12N 11/00; C12N 11/02
[52] U.S. Cl. .......................... 424/450; 435/174; 435/177
[58] Field of Search ............................ 424/450; 435/174, 435/177

[56] References Cited

FOREIGN PATENT DOCUMENTS

| | | |
|---|---|---|
| 55-118415 | 9/1980 | Japan . |
| 57-43688 | 3/1982 | Japan . |
| 59-213392 | 12/1984 | Japan . |
| 64-47381 | 2/1989 | Japan . |
| 2-135092 | 5/1990 | Japan . |

OTHER PUBLICATIONS

"Experiment 48—Assay of β-Galacosidase", Miller, Experiments in Molecular Genetics, (1972), pp. 352–355.
"Protein Determination in Membrane and Lipoprotein Samples: Manual and Automated Procedures", Markwell et al, Methods in Enzymology, vol. 72, (1981), pp. 296–303.
"Evaluation of a New Liposome Preparation Technique, the Freeze–Thawing Method, Using L–Asparaginase as a Model Drug", Ohsawa et al, Chem. Par. Bull., vol. 33, No. 7, (1985), pp. 2916–2923.
"Assay for Nanogram Quantities of DNA in Cellular Homogenates", Brunk et al, Analytical Biochemistry, vol. 92, (1979), pp. 497–500.
"Selection for Animal Cells that Express the Escherichia Coli Gene Coding for Xanthine–Guanine Phosporibosyltransferase", Mulligan et al, Proc. Nat'l. Acad. Sci. USA, vol. 78, No. 4, Apr. 1981, pp. 2072–2076.
"Liposome Preparation: Methods and Mechanism" David W. Deamer and Paul S. Uster/University of California at Davis, Davis, California.
"Entrapment of High–Molecular–Mass DNA Molecules in Liposomes for the Genetic Transformation of Animal Cells", Szelei et al, Biochem. J., vol. 259, (1989), pp. 549–553.

"Liposomes as Carriers for Intracellular Delivery of Nucleic Acids", Straubinger et al, Methods in Enzymology, vol. 101, (1983), pp. 512–527.
"A Novel Method for Preparing Liposome with a High Capacity to Encapsulate Proteinous Drugs: Freeze–Drying Method", Ohsawa et al, Chem. Pharm. Bull., vol. 32, No. 6, (1984), pp. 2442–2445.
"Solute Distributions and Trapping Efficiencies Observed in Freeze–Thawed Multilamellar Vesicles", Mayer et al., Biochimica et Biophysica Acta, vol. 817, (1985), pp. 193–196.
"Trapping Drug Efficiency in Liposomes Produced by Extrusion of Freeze–Thaw Multilamellar Vesicles", Alino et al., Biochem. Soc. Trans., vol. 17, (1989), pp. 1000–1001.
"Introduction of Liposome–Encapsulated SV40 DNA into Cells", Fraley et al, The Journal of Biological Chemistry, vol. 255, No. 21, Nov. 10, 1980, pp. 10431–10435.
"Liposomes as Gene Carriers: Efficient Transformation of Mouse L Cells by Thymidine Kinase Gene", Ridder et al, Science, vol. 215, Jan. 8, 1982, pp. 166–168.
"In vivo Expression of Rat Insulin After Intravenous Administration of the Liposome–Entrapped Gene for Rat Insulin I", Nicolau et al, Proc. Nat'l. Acad. Sci. USA, vol. 80, Feb. 1983, pp. 1068–1072.
"Liposome–Mediated Transfer of Simian Virus 40 DNA and Minichromosome into Mammalian Cells", Rizzo et al, J. Gen. Virol., vol. 64, (1983), pp. 911–918.
"A Simple and Efficient Liposome Method for Transfection of DNA into Mammalian Cells Grown in Suspension", Itani et al, Gene, vol. 56, (1987), pp. 267–275.
"Liposome Bearing a Quaternary Ammonium Detergent as an Efficient Vehicle for Functional Transfer of TMV–RNA into Plant Protoplasts", Ballas et al., Biochimica et Biophysica Acta, vol. 939, (1988), pp. 8–18.
Koshizaka et al., Novel Liposomes for Efficient Transfection of B–Galactosidase Gene into COS–1 . . . , pp. 185–192, (1989).
"Entrapment of Plasmid DNA by Liposomes and Their Interactions with Plant Protoplasts", Lurquin, Nucleic Acids Research, vol. 6, No. 12, (1979), pp. 3773–3784.
"Liposome–Mediated Association of DNA with Plant Protoplasts: Influence of Vesicle Lipid Composition", Rollo et al., Dev. Plant Biol., vol. 5, (1980), pp. 237–246.

(List continued on next page.)

*Primary Examiner*—John W. Rollins
*Assistant Examiner*—Deborah K. Ware
*Attorney, Agent, or Firm*—Nikaido, Marmelstein, Murray & Oram LLP

[57] ABSTRACT

For increasing gene entrapping efficiency, it is preferable that liposome membrane to be formed is positively charged. For this purpose, a lipid with quaternary amine has been employed as one of constitutional lipids, but the such lipid may show toxicity to cells to be transformed with the gene for expression. The invention selects, as constitutional lipids for liposomes, N-(α-trimethylammonioacetyl)-didodecyl-D-glutamate chloride (TMAG), dilauroylphosphatidylcholine (DLPC), and dioleoylphosphatidylethanolamine (DOPE) with molar ratio of 1:2:2, and vortex treatment for preparing the liposomes with multi-layers to entrap the gene therein.

4 Claims, 1 Drawing Sheet

OTHER PUBLICATIONS

"Quantitative Aspects of Nucleic Acids Sequestration in Large Liposomes and Their Effects on Plant Protoplasts", Lurquin et al., FEBS Letters, vol. 125, No. 2, Mar. 1981, pp. 183–187.

"Lipofection: A Highly Efficient, Lipid–Mediated DNA–Transfection Procedure", Felgner et al, Proc. Nat'. Acad. Sci. USA, vol. 84, Nov. 1987, pp. 7413–7417.

"Use of a Quaternary Ammonium Detergent in Liposome Mediated DNA Transfection of Mouse L–cells", Pinnaduwage et al, Biochimica et Biophysica Acta, vol. 985, (1989), pp. 33–37.

LIPOSOME FOR ENTRAPPING GENE, LIPOSOMAL PREPARATION AND PROCESS FOR THE MANUFACTURE OF THE PREPARATION

This application is a continuation application of U.S. Ser. No. 08/084,629, filed Jun. 30, 1993, now abandoned, which is a divisional application of U.S. Ser. No. 07/750,125, filed Aug. 26, 1991, now abandoned.

BACKGROUND OF THE INVENTION

1. Field of the Invention

The present invention relates to liposomes, and more particularly multilamellar vesicles for entrapping a gene, a gene entrapping liposomal preparation, and a process for the manufacture of the liposomal preparation.

2. Related Arts

The liposomes are lipid vesicles, have similar structure as cell membranes in the living body, and can be prepared by suspending a polar lipid film in a solvent. The liposomes have been classified from morphological and structural view points into (1) multilamellar vesicles (MLV, liposomes with multilayers), (2) small unilamellar vesicles (SUV, small liposomes with a single layer), and (3) large unilamellar vesicles (LUV, large liposomes with a single layer).

The liposomes can entrap in inner space and membrane layer thereof various materials from low molecular substances to high molecular substances such as nucleic acid, protein or the like. Therefore, techniques utilizing the liposomes as a vehicle or carrier for introduction of the gene into a mammalian or vegetable cell have been developed, for instance, as shown in the following literatures.

a) P. F. Lurquin "Nucleic Acids Res.", Vol. 6, page 3773 (1979);

b) R. Franco et al "Dev. Plant Biol.", Vol. 5, page 237 (1980);

c) P. F. Lurquin et al "FEBS Lett.", Vol. 125, page 183 (1981);

d) Jap. Pat. No. Sho 57 (year of 1982)—43688(A);

e) P. L. Felgner et al "Proc. Natl. Acad. Sci. USA", Vol. 84, page 7413 (1987);

f) P. Pinnaduwage et al "Biochim. Biophys. Acta", Vol. 985, page 33 (1989);

g) R. Fraley et al "J. Biol. Chem.", Vol. 255, page 10431 (1980);

h) Jap. Pat. No. Sho 55 (year of 1980)—118415(A);

i) M. S. Ridder et al "Science", Vol. 215, page 166 (1982);

j) C. Nicolau et al "Proc. Natl. Acad. Sci. USA", Vol. 80, page 1068 (1983);

k) W. B. Rizzo et al "J. Gen. Virol.", Vol. 64, page 911 (1983);

l) Jap. Pat. No. Sho 59 (year of 1984)—213392(A);

m) T. Itani et al "Gene", Vol. 56, page 267 (1987);

n) N. Ballas et al "Biochim. Biophys. Acta", Vol. 939, page 8 (1988);

o) J. Szelei et al "Biochem. J.", Vol. 259, page 549 (1989);

p) Jap. Pat. No. Sho 64 (year of 1989)—47381(A); and q) Jap. Pat. No. Hei 2 (year of 1990)—135092(A).

However, it has been reported that the MLV which are most easy in preparation may give to DNA a damage of nick or the like during a stage of operation for introducing the gene DNA into the liposomes (see said Literature a) and that the MLV are not suitable for entrapping DNA, since an entrapping or catching efficiency on high molecular substances is low [R. M. Straubinger and Papahajopoulos "Methods in Enzymol.", Vol. 101, page 512 (1983)]. The SUV are also not suitable for entrapping the gene and the like nucleic acid, since sonication for preparing the liposomes may give a damage to the nucleic acid, and inner space thereof is small. While, it has been considered that the LUV are suitable for entrapping the nucleic acid or the like, since inner space thereof is larger than that of said MLV and SUV, and an operation for preparing the same shall not give significant damage to DNA, but all of processes for preparing LUV, namely a reverse phase evaporation method, an ether injection method. $Ca^{2+}$ fusion method and the like require quite complicate and troublesome operations and thus it cannot be said, at the present time, that such a process is suitable for an industrial large scale production.

It was actual situation that an entrapping efficiency of nucleic acid or the like with negative charge becomes low, when the membrane of liposomes has no charge or has been negatively charged, and that an expression efficiency of cells transformed with such gene entrapping liposomes cannot be made so higher. Therefore, such techniques have been developed that a positively charged lipid is added for constitutional lipids of the liposomes, or a surface active agent or the like is added for accelerating the entrapping of nucleic acid due to an electrostatic binding force to increase the entrapping efficiency. For instance, following reports have been issued. A primary amine of stearylamine is added for preparing liposomes to increase an entrapping efficiency of nucleic acid and to attain a relatively high resistibility to deoxyribonuclease, so that a gene can be introduced into *Escherichia coli* or a protoplast (see said Literatures b and c). Good nucleic acid entrapping efficiency can also be attained to show quite high introduction efficiency into cells, in comparison with widely accepted calcium phosphate precipitation method, when a quaternary amine which is more basic than the primary amine is employed (see said Literatures e, f and n).

The present inventors have also made apparent in Jap. Pat. No. Hei 2-135092(A) (said Literature q) that the gene entrapping efficiency has correlation with basicity of lipid with positive charge, and that addition of a quaternary amine for preparing liposomes is more effective than that of a secondary or tertiary amine on introduction or gene into cells.

SUMMARY OF THE INVENTION

Taking the matters as discussed above into consideration, it is preferable to select a lipid with not a primary, secondary or tertiary amine, but a quaternary amine, as one of constitutional lipids of the liposomes.

However, when the lipid with quaternary amine has been selected as one of constitutional lipids for the liposomes, the lipid shows a toxicity to the cells wherein a gene is to be introduced for transformation thereof and may kill the cells. This has constituted a great neck or disadvantage for introducing gene entrapped in liposomes into the cells.

Therefore, the problem which the invention aims to dissolve lies in excluding such a disadvantage.

A first concrete object of the invention lies in providing liposomes which can easily be prepared to allow a large-scale production thereof, has high gene entrapping efficiency to show good expression of the gene in cells, and shows little or no toxicity to cells.

A second concrete object of the invention lies in providing a liposomal preparation, wherein a gene has been entrapped in large amount.

A third concrete object of the invention lies in providing a process for the easy manufacture of the liposomal preparation.

According to the invention, the aforesaid problem can be dissolved by a multilamellar liposome for entrapping gene, characterized in that the lipids constituting the liposome consist essentially of N-(α-trimethylammonioacetyl) -di-dodecyl-D-glutamate chloride (TMAG), dilauroylphosphatidylcholine (DLPC), and dioleoylphosphatidylethanolamine (DOPE), and that molar ratio of the lipids is 1:2:2, to attain the first object.

The second object can be attained by a liposomal preparation, in which a gene is entrapped by the multilamellar liposome.

The third object can tie attained by preparing the gene entrapping multilamellar liposomes through a vortex treatment.

The TMAG to be used for preparing the multilamellar liposomes according to the invention is the quaternary amine described in Jap. Pat. No. Hei 2-135092 (Literature q). There is no limitation for the multilamellar liposomes in size thereof and number of layers constituting lipid membrane. In the process for the manufacture of the multilamellar liposomal preparation according to the invention, the vortex treatment is recommended, as above, on following grounds. For preparing MLV which can entrap nucleic acid, protein or the like high molecular substance, various processes employing a freeze-dry method, freeze-thawing method and the like have been proposed [T. Ohsawa et al "Chem. Pharm. Bull.", Vol. 32, page 2442 (1984); L. D. Mayer et al "Biochim. Biophys. Acta", Vol. 817, page 193 (1985); S. F. Alino et al "Biochem. Soc. Trans.", Vol. 17, page 1000 (1989) and others]. Therefore, the inventors have prepared various liposomes, in which a gene DNA is entrapped, namely MLV prepared with use of the freeze-dry method, MLV with the freeze-thawing method, and MLV through the vortex treatment, and check and compare the gene entrapping efficiency, resistibility to deoxyribonuclease, and gene transfection efficiency in cells, to find that all of liposomes show the gene entrapping efficiency and the resistibility in same level, but the gene transfection efficiency of the MLV prepared through the vortex treatment is far excellent than those of the other MLVs prepared by the freeze-dry or freeze-thawing method.

As aforesaid, the most serious problem on conventional liposomes containing the lipid with quaternary amine lies in that the lipid shows a toxicity to cells wherein the gene entrapping liposomes are to be introduced for transformation thereof.

Therefore, the inventors have carried out experiments for checking a toxicity of the liposomes according to the invention to cells, namely by adding the multilamellar liposomes of the invention into a medium containing COS-1 cells to make contact therewith for 72 hours. Surprisingly, the MLV according to the invention have little toxicity. LUV of same lipid composition and concentration shows 1.7-folds toxicity compared with that for the MLV according to the invention.

Reagent for preparing SUVs for introducing a gene and containing the lipid with quaternary amine has been developed by P. L. Felgner et al (Literature e) and marketed under trademark of "Lipofectin". Therefore, the inventors have carried out an experiment similar to the above on the Lipofectin liposome to find that this SUV shows the toxicity of 1.8–3.5 folds, in comparison with the MLV according to the invention, when a concentration of lipids was set in the same level.

For introducing of gene into cells with good efficiency, it is necessary to make sufficiently contact the MLV according to the invention with the cells. However, an optimum contacting period of time is different depending on a kind of cells in which the gene should be introduced. Therefore, it is preferable to set the optimum period of time by preliminary experiments.

DETAILED DESCRIPTION OF THE PREFERRED EMBODIMENTS

Figure 1:
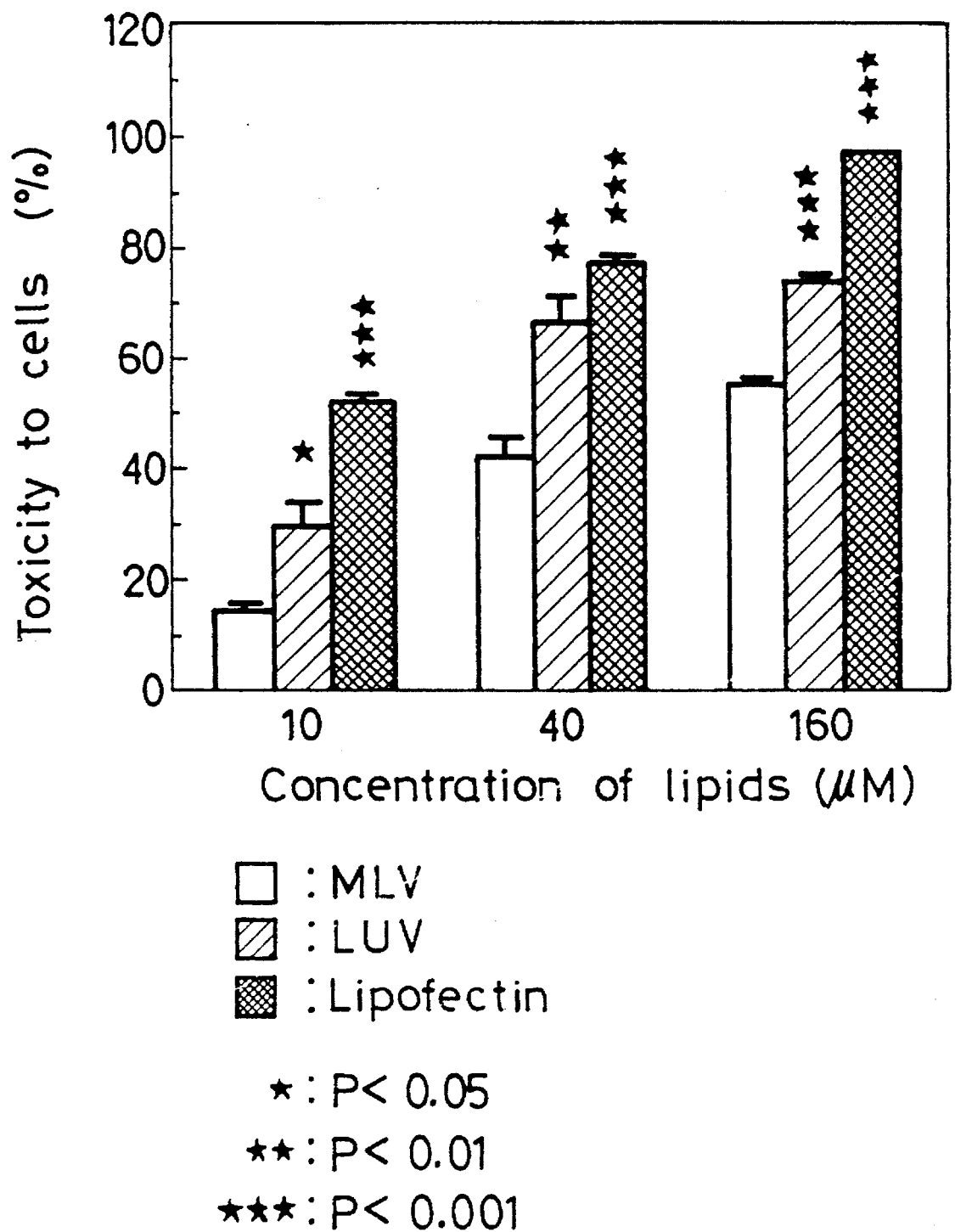
FIG. 1 is a graph showing results of tests which check a toxicity of MLV according to the invention, LUV prepared by conventional reverse phase evaporation method, and commercial SUV marketed under trade mark of "Lipofectin", to COS-1 cells.

The invention will now be further explained with reference to Examples, Reference Examples and Test Examples.

Materials and analytical methods referred to in the Examples and others are as follows.

(a)  N-(α-Trimethylammonioacetyl)-didodecyl-D-glutamate chloride (TMAG): Marketed by Sougo Yakkou Kabushiki Kaisha of Japan.

(b) Dilauloylphosphatidylcholine (DLPC) and Dioleoylphosphatidylethanolamine (DOPE): Marketed by Sigma Chemical Co. of St. Louis, Mo., U.S.A.

(c) pCH110 plasmid and pMSG CAT plasmid: Marketed by Pharmacia Fine Chemicals AB of Uppsala, Sweden.

(d) COS-1 cell (ATCC No. CRL-1650), CV-1 cell (ATCC No. CCL-70), and NIH/3T3 cell (ATCC No. CRL-1658): Marketed by Dainippon Pharmaceutical Co., Ltd. of Osaka. Japan.

(e) Lipofectin: Marketed by Bethesda Research Laboratories Life Technology Co. of Maryland, U.S.A.

(f) CAT assay kit and calcium phosphate transfection kit: Marketed by 5-prime-3-prime Inc. of West Chester, Pa., U.S.A.

(g) Determination of β-galactosidase activity: The activity was determined, in accordance with the method described in "Experiments in Molecular Genetics", page 352, published by Cold Spring Harbor, New York, N.Y., U.S.A. (1972).

(h) Determination of protein in cell extract: The protein content was determined, in accordance with the method described in "Methods in Enzymol.", Vol. 72, page 296 (1981).

EXAMPLE 1

A liposomal preparation which constitutional lipids are TMAG, DLPC and DOPE, molar ratio thereof being 1:2:2 and entrapping DNA was prepared as described below. 0.2 µmol of TMAG, 0.4 µmol of DLPC, and 0.4 µmol of DOPE were dissolved in chloroform and charged in a cone test tube, inner surface of which was previously silylated. The solvent of chloroform was removed with a rotary evaporator under a reduced pressure to form a lipid film (total lipid amount: 1 µmol) and to dry the same in vacuo. Then 20 µg of phage λ DNA in 300 µl of phosphate buffered saline (PBS, pH 7.4) were added in the test tube, and the resulting solution was shaken for 2 minutes with a vortex mixer to obtain DNA entrapping multilamellar liposomes (MLV). DNA not entrapped by the liposomes was removed by utilizing a density gradient-centrifugal method with Ficoll-Paque (5.7 g Ficoll 400 and 9 g sodium diatrizoate in 100 ml, Ficoll 400 is a high molecular weight hydrophobic polymer of sucrose obtained by copolymerizing sucrose with epichlorohydrin). An analysis by agarose gel electrophoresis of the DNA in the desired MLV showed no damage in DNA.

COMPARATIVE EXAMPLE 1

MLVs entrapping phage λ DNA were prepared by utilizing freeze-dry method or freeze-thawing method, as stated below.

The MLV according to the freeze-dry method were prepared in accordance with the method as described in "Chem. Pharm. Bull.", Vol. 32, page 2442 (1984).

The MLV according to the freeze-thawing method were prepared in accordance with the method as described in "Chem. Pharm. Bull.", Vol. 33, pages 2916 (1985).

In both cases, lipid concentration, lipid composition and DNA concentration were set as the same with those in Example 1.

TEST EXAMPLE 1

In preparation of liposomes in Example 1 and Comparative Example 1, a proportion of DNA amount entrapped in the liposomes to an amount of added DNA was measured to determine entrapping efficiency.

On the DNA entrapped by the liposomes obtained in Example 1 and Comparative Example 1 further, resistibility of the DNA to deoxyribonuclease was measured, in accordance with the method as described in "Proc. Natl. Acad. Sci. USA", Vol. 80. page 1068 (1983). Namely, a decomposition ratio of DNA with deoxyribonuclease was measured by using a definite amount of liposomes, which were treated the same with deoxyribonuclease for 1 hour at 37° C. in the presence of magnesium chloride, and then added a mixed solution of 1.5M sodium chloride and 30 mM EDTA. Then a mixed solution of chloroform and methanol (2:1, v/v) was added to remove lipids and recover the DNA, and the amount of DNA was measured in accordance with the method described in "Anal. Biochem.", Vol. 92, page 497 (1979).

Results are shown in the following Table 1. As apparently seen therefrom, the decomposition ratio and entrapping efficiency of the DNA in each liposome obtained by Example 1 and Comparative Example 1 are in substantially the same level.

TABLE 1

| Sample of Liposomes | Decomposition ratio | Entrapping efficiency |
|---|---|---|
| Example 1 | 7.70% | 99.3% |
| Freeze-dry method | 4.94% | 97.5% |
| Freeze-thawing method | 18.0% | 100% |

REFERENCE EXAMPLE 1 AND REFERENCE TEST EXAMPLE 1

Introduction of gene into cells, using gene entrapping MLV prepared by freeze-dry method MLVs were prepared by using 1 μmol of lipids (TMAG, DLPC and DOPE, molar ratio of 1:2:2) and according to the freeze-dry method as described in Comparative Example 1, the MLV entrapping pCH110 plasmid (20 μg) which has an insert of β-galactosidase gene of *Escherichia coli*.

Further, LUVs as liposomes different from the MLV in membrane layer structure were prepared with use of the reverse phase evaporation method as described in Jap. Pat. No. Hei 2- 135092 (Literature q) and under the same conditions with the above.

COS-1 cells ($1 \times 10^5$) were cultured in Dalbecco's modified Eagle's medium (2 ml) supplemented with 10% fetal calf serum in 35 mm-culture dish. After 16 hours, the medium was exchanged with fresh one. The MLVs (or LUVs) entrapping pCH110 plasmid of 0.5 μg in total were added, 7 hours after the medium exchange, and 16 hours after the addition of the liposomes, the medium was exchanged with fresh one. After 72 hours from the second medium exchange, the medium was removed from the culture dish and cells were washed with 2 ml of PBS. After the addition of 1 ml of PBS into the culture dish, the cells were scraped off with a rubber policeman and gathered into a sample tube to centrifuge the same at 14000 rpm for 2 minutes, and then a supernatant was discarded. After suspended the cells in 0.2–0.3 ml of PBS, alternative freezing (−76° C.)—thawing (+37° C.) operation was repeated three times, and then centrifuged at 14000 rpm for 5 minutes to recover a supernatant as a cell extract. The activity of β-galactosidase was measured for the cell extract.

As a control, another gene introduction test was carried out by utilizing calcium phosphate precipitation method including a step of treatment with glycerol.

Results are shown in following Table 2. It is apparent therefrom that the activity of β-galactosidase expressed in the case of using the MLV prepared by freeze-dry method is about ⅙ in comparison with that in the case of using the LUV prepared by the reverse phase evaporation method, and is about ⅓, in comparison with that in the case of utilizing the calcium phosphate precipitation method.

TABLE 2

| Gene introduction method | Activity (nmol/min/ml) |
|---|---|
| Calcium phosphate precipitation method | 65.4 |
| LUV utilizing method | 125.8 |
| MLV utilizing method (Freeze-dry method) | 22.0 |

EXAMPLE 2 AND TEST EXAMPLE 2

Gene insertion

MLVs entrapping 20 μg of pCH110 plasmid were prepared with use of lipids (1 μmol, TMAG:DLPC:DOPE= 1:2:2) through the vortex treatment and in accordance with the method described in Example 1.

As a control liposome, gene entrapping LUVs were prepared with the lipids of the same in concentration and composition with the above, but by utilizing the reverse phase evaporation method.

A gene introduction into cells was carried out with use of each of said MLV and LUV. Operations of gene introduction are same with those described in Reference Example 1 and with use of 0.5 μg of pCH110 plasmid to COS-1 cells ($1 \times 10^5$).

As a control gene introduction method, the calcium phosphate precipitation method was also carried out.

Results are shown in the following Table 3. As apparently seen therefrom, the MLV prepared through the vortex treatment showed an gene introduction efficiency in the same level with the LUV prepared by the reverse phase evaporation method, and the gene introduction method with use of the MLV is excellent than the calcium phosphate precipitation method.

TABLE 3

| Gene introduction method | Activity (nmol/min/ml) |
| --- | --- |
| Calcium phosphate precipitation method | 83.6 |
| LUV utilizing method | 149.8 |
| MLV utilizing method | 137.3 |

EXAMPLE 3 AND TEST EXAMPLE 3

MLVs were prepared by using lipids (1 μg, TMAG:DLPC:DOPE=1:2:2) through the vortex treatment according to the method described in Example 1, but the liposomes entrapping 20 μg of pMSG CAT plasmid which has an insert of chloramphenicolacetyltransferase (CAT) gene.

With use of this gene entrapping MLV, an introduction of the gene into cells was carried out. Since the CAT gene is arranged in the pMSG CAT plasmid at downstream of mouse mammary tumor virus LTR (MMTV-LTR) promoter, expression of which is controlled by dexamethasone or the like glucocorticoid, dexamethasone was added to a medium to measure an activity of expressed CAT.

Introducing operations are as follows. In a culture dish (dia.: 35 mm) containing Dalbecco's modified Eagle's medium (2 ml) supplemented with 10% fetal calf serum, NIH/3T3 cells ($1 \times 10^5$) were incuvated the same. After 16 hours, the medium was exchanged with a fresh one. After 8 hours from the medium exchange, the MLVs entrapping pMSG CAT plasmid of 0.5 μg in total were added. After 16 hours from the addition of the liposomes. the liposomes were removed and the medium was exchanged with the fresh one. Dexamethasone in ethanol was added into the culture dish, so that its concentration becomes 1 μM. After incuvated for 48 hours, the cells were collected to prepare a cell extract for measuring the activity of expressed CAT, as in Reference Example 1.

As a control, another type gene introduction of the calcium phosphate precipitation method was carried out.

Results are shown in the following Table 4. As apparently seen therefrom, the gene introduction into the cells with use of MLV prepared through the vortex treatment showed an expression of about 6 folds than that in the calcium phosphate precipitation method.

TABLE 4

| Gene introduction method | Activity of CAT (pg/ml) |
| --- | --- |
| Calcium phosphate precipitation method | 38.2 |
| MLV utilizing method | 224.5 |

EXAMPLE 4 AND TEST EXAMPLE 4

In the Examples and others given above, gene introduction efficiencies were compared through one transient expression, wherein gene expresses in the host cell within several days.

In this Example, while, investigations were directed to an establishment of a cell-line, wherein DNA of the cell has an insert of a gene to permanently express the gene.

As the plasmid with an insert of gene, pMSG CAT plasmid was selected as in Example 3, and as the host cell, CV-1 cell was selected. Since the pMSG CAT plasmid has xanthine guanine phosphoribosyltransferase gene of *Escherichia coli* (Eco gpt), at downstream of SV40 promoter, transformation thereof was carried out under gpt selective conditions as described in "Proc. Natl. Acad. Sci. USA", Vol. 78, page 2072 (1981). MLVs entrapping 20 μg of pMSG CAT plasmid were prepared with use of lipids (1 μmol, TMAG:DLPC:DOPE=1:2:2) and in accordance with the method as described in Example 1. As a control liposome entrapping the plasmid. Lipofectin liposome was selected, since the Lipofectin liposome has a lipid with quaternary amine other than TMAG, as one of constitutional lipids.

A gene introduction into the cells was carried out with use of the MLVs or Lipofectin liposomes, as gene carrier. As a control, a gene introduction was carried out by calcium phosphate precipitation method.

Operations for introducing gene into the cells were carried out, as follows. CV-1 cells ($1 \times 10^5$) were cultured in Earle's minimum essential medium (EMEM, 2 ml) supplemented with 10% fetal calf serum to incuvate the same in 35 mm-culture dish. On the next day, the medium was exchanged with the fresh one, added MLV or Lipofectin liposomes entrapping the DNA (1 μg). and incuvated further for 19 hours. As to gene introduction with the calcium phosphate precipitation method, a mixture of the DNA and calcium phosphate was added to the cells to incuvate for 4 hours, treated with glycerol for 2 minutes at room temperature, and then incuvated similarly to the above liposome utilizing methods. Then, the medium was exchanged with the fresh one to continue the incuvation for 2 days. Thereafter, the cells were treated with trypsin to scrape-off the same from the culture dish, gathered, washed with a growing medium, diluted to 10 folds, and incuvated again in a medium. After 2 days, the medium was changed with gpt selective medium. The pgt selective medium was exchanged with the fresh one with 3 days interval. On 15th day after gene introduction, the cells were washed with PBS, fixed with 20% neutrally buffered formalin solution, and dyed with 0.05% methylene blue to count the number of colonies.

Results are shown in the following Table 5. It is apparent therefrom that the number of colonies of the cell transformed with gene entrapping MLV according to the invention reaches about 6 folds. In comparison with the cases of utilizing the Lipofectin liposomes and the calcium phosphate precipitation method.

TABLE 5

| Gene Introduction method | Number of transformed colonies |
| --- | --- |
| Calcium phosphate precipitation method | 20.9 ± 2.1 |
| Lipofectin utilizing method | 27.3 ± 2.7 |
| MLV utilizing method | 173.7 ± 3.0 |

EXAMPLE 5 AND TEST EXAMPLE 5

Toxicity to cells

MLV and LUV were prepared, which liposomes consist of constitutional lipids of TMAG, DLPC and DOPE in molar ratio of 1:2:2 and entrap no gene. Among the liposomes, the MLV was prepared by adding 1.5 ml of PBS to the lipid film (4 μmol) with the above lipid composition, and through the vortex treatment in accordance with the method as described in Example 1. While, the LUV was prepared with use of the lipid film same with that for MLV in its lipid composition and amount, but by utilizing the reverse phase evaporation method as described in Jap. Pat. No. Hei 2-135092 (Literature q). As a control , Lipofectin liposomes were prepared with use of commercially available Lipofectin reagents.

An evaluation was given based on dye-uptake method. Namely, In a 24 hole-culture plate, each hole of which contains Dalbecco's modified Eagle's medium (0.4 ml) supplemented with 10% fetal calf serum, COS-1 cells ($2\times10^4$) were inoculated and incuvated for 20 hours in an incuvator under conditions of 37° C. and 5% $CO_2$. Then, the medium was exchanged with the fresh one and 100 μl of liposome solution In various lipid concentrations were added therein. After incuvated for 72 hours, the medium was removed, and the cells were washed with PBS, fixed with 10% neutrally buffered formalin solution, and dyed with 0.05% methylene blue dyeing solution. After removed excess methylene blue solution, the dye taken into the cells was extracted with 0.33M hydrochloric acid solution to measure an absorbance at 665 nm. By calculating a ratio of absorbance In the test sample to that in a control sample, an inhibition of cell growth was evaluated.

Results are shown in FIG. 1 (In the Figure, the significant is given by comparing with the corresponding MLV). It is apparently seen therefrom that the MLV according to the invention showed a low toxicity to the cell, with significant difference, in any lipid concentration, when compared with the LUV which has the same lipid composition and concentration with that for the MLV.

The lipofectin liposome showed a higher toxicity of 1.8–3.5 folds than the toxicity of the MLV according to the invention.

We claim:

1. A process for producing a deoxyribonucleic acid entrapping multilamellar liposome, comprising the following steps:

dissolving lipids of N-(α-trimethylammonioacetyl)-didodecyl-D-glutamate chloride, dilauroylphosphatdylcholine and dioleophosphatidylethanolamine in a molar ratio of 1:2:2, in a solvent suitable for forming a lipid film, removing the solvent with an evaporator to form a lipid film, adding a deoxyribonucleic acid solution to said lipid film to form a mixture, and shaking said mixture with a vortex mixer to form a deoxyribonucleic acid entrapping multilamellar liposome.

2. The method according to claim 1, wherein said evaporator is a rotary evaporator.

3. The method according to claim 1, wherein said solvent is chloroform.

4. The method according to claim 1, further comprising separating any deoxyribonucleic acid not entrapped in the liposome using a density gradient centrifugal method with Ficoll-Paque.

* * * * *